US007190762B2

United States Patent
He

(10) Patent No.: US 7,190,762 B2
(45) Date of Patent: Mar. 13, 2007

(54) SCANNING LINE DETECTOR FOR TWO-DIMENSIONAL X-RAY DIFFRACTOMETER

(75) Inventor: Bob Baoping He, Madison, WI (US)

(73) Assignee: Broker AXS, Inc, Madison, WI (US)

( * ) Notice: Subject to any disclaimer, the term of this patent is extended or adjusted under 35 U.S.C. 154(b) by 0 days.

(21) Appl. No.: 10/977,251

(22) Filed: Oct. 29, 2004

(65) Prior Publication Data

US 2006/0093090 A1     May 4, 2006

(51) Int. Cl.
  *G01N 23/20*     (2006.01)
(52) U.S. Cl. .......................................... 378/70; 378/71
(58) Field of Classification Search .................. 378/70, 378/71, 73, 75, 79, 81, 82, 83, 84, 119, 121, 378/125, 127, 132, 133, 143, 144
See application file for complete search history.

(56) References Cited

U.S. PATENT DOCUMENTS

| 4,475,225 | A |   | 10/1984 | Galy et al. ..................... 378/88 |
| 5,373,544 | A | * | 12/1994 | Goebel .......................... 378/71 |
| 5,446,777 | A |   | 8/1995  | Houtman ....................... 378/45 |
| 6,748,048 | B2 | * | 6/2004  | Dosho ........................... 378/79 |
| 6,751,287 | B1 | * | 6/2004  | Kalyon et al. ................. 378/71 |
| 2005/0105684 | A1 | * | 5/2005 | Bruegemann et al. ........ 378/71 |
| 2005/0190881 | A1 |   | 9/2005 | Obata et al. ................... 378/87 |

FOREIGN PATENT DOCUMENTS

JP             11006806 A      1/1999

OTHER PUBLICATIONS

He, Bob, "Introduction to Two-Dimensional X-Ray Diffraction", Powder Diffraction, vol. 18, No. 2, Jun. 2003, pp. 71-85, USA.

* cited by examiner

*Primary Examiner*—Courtney Thomas
(74) *Attorney, Agent, or Firm*—The Law Offices of Paul E. Kudirka

(57) ABSTRACT

A scanning line detector according to the present invention uses a detector with a linear arrangement of detection elements that is moved along a range of diffracted x-ray directions to collect data across a multidimensional detection area. The scanning line detector allows for the simulation of a two-dimensional detector system without the need for a two-dimensional detector. The detector may follow a desired path to simulate a desired shape, such as a cylinder. A slit may be included to limit the detector line width, and a scatter shield may be used to minimize noise from air-scattered x-rays. The detector may also use a specially designed monochromator for conditioning the diffracted x-rays. The detector may be rotatable about an axis parallel to a direction along which x-rays are diffracted, allowing it to be used in different orientations.

25 Claims, 5 Drawing Sheets

SCANNING LINE DETECTOR FOR TWO-DIMENSIONAL X-RAY DIFFRACTOMETER

FIELD OF THE INVENTION

This invention relates, generally, to the field of x-ray diffraction analysis and, more specifically, to detection of diffracted x-ray energy in two dimensions.

BACKGROUND OF THE INVENTION

Two-dimensional x-ray diffraction refers to x-ray diffraction applications with a two-dimensional diffraction image and corresponding data reduction and analysis. A two-dimensional diffraction pattern contains far more information than a one-dimensional profile collected with a conventional diffractometer. In recent years, usage of two-dimensional (2D) detectors has dramatically increased due to advances in detector technology, point beam x-ray optics, and computing power. A two-dimensional diffractometer is a diffraction system with the capability of acquiring a diffraction pattern in two-dimensional space and analyzing 2D diffraction data accordingly. A typical two-dimensional diffractometer system 10 normally consists of five major units as shown in FIG. 1. An X-ray generator 12 produces x-rays with the required radiation energy, focal spot size and intensity. X-ray optics 14 condition the primary x-ray beam to the required wavelength, beam focus size, beam profile and divergence. A goniometer and sample stage 16 establish and maneuver the geometric relationship between primary beam, sample and detector. A sample alignment and monitoring system 18 assists users in positioning the sample at the instrument center and monitoring the sample state and position. And a two-dimensional detector 20 intercepts and records the x-rays scattered from a sample and, along with a processing unit, saves and displays the diffraction pattern into a two-dimensional image frame.

Another method of collecting diffraction data uses a point detector that is scanned around the sample along a detection circle. FIG. 2 is a schematic view of a method of x-ray diffraction from a powder (polycrystalline) sample. The figure shows graphically a conical distribution of diffracted x-ray energy. For simplicity, the figure shows only two diffraction cones, one representing forward diffraction (2θ<90°) and one representing backward diffraction (2θ>90°). In actuality, the diffraction pattern from the polycrystalline sample forms a series of diffraction cones, assuming a large number of crystals are oriented randomly in the space are covered by the incident x-ray beam. Each diffraction cone corresponds to the diffraction from the same family of crystalline planes in all the participating grains.

The diffraction measurement in a conventional diffractometer is confined within a plane, here referred to as the diffractometer plane 22. In FIG. 2, a point detector 24 makes a 2θ scan along a detection circle 26 located within the diffractometer plane. At points all along the circle, the detector 24 detects the diffracted x-rays. This information is assembled to provide an indication of the diffraction pattern along the detection circle. Thus, the diffraction profile covers only the diffraction intensity variation within the diffractometer plane. Since the diffraction data out of the diffractometer plane is not detected, this additional information is either ignored, or is measured by various additional scans with the sample in different orientations.

SUMMARY OF THE INVENTION

In accordance with the present invention, an x-ray diffraction system is provided for analyzing a sample so as to provide two-dimensional diffraction data using a one-dimensional line detector. The system includes a source of x-ray energy that is directed toward the sample, and an x-ray detector that has an elongate shape. The shape of the detector is such that individual detection elements of the detector are arranged substantially linearly. The detector is also movable substantially perpendicularly to directions along which x-ray energy is diffracted by the sample so as to collect x-ray diffraction data across a multidimensional space.

In one embodiment, the detection elements of the detector are arranged in a substantially straight line, although other shapes are also possible. As the line detector is scanned along in a direction perpendicular to the long dimension of the detector, data is collected in two dimensions without the need for a two-dimensional detector. The sample may lie in a diffractometer plane, and the detector can follow a path that is parallel to the diffractometer plane. Variations are possible in the movement and positioning of the detector. The detector may be positioned relatively close to the sample, so as to provide large angular coverage, or may be positioned further from the sample, so as to provide better angular resolution. The detector may also trace out a particular desired shape, such as a cylinder, so as to simulate a desired surface detector. Moreover, the detector may be positioned in a different rotational orientation about an axis parallel to a direction along which x-ray energy is diffracted, and the detector then moved along the scanning direction with the detector in that rotational orientation.

Other features may be provided with the present invention. A slit may be positioned in front of the detection elements of the detector that limits the detection line width. Similarly, a scatter shield may be provided that moves with the detector and shields it from scattered x-ray energy along directions outside of a selected x-ray diffraction range. A monochromator may also be provided that redirects diffracted x-ray energy from the sample to the detector. The monochromator, which may be a multilayer mirror, limits the redirected x-ray energy to a predetermined wavelength range.

BRIEF DESCRIPTION OF THE DRAWINGS

The above and further advantages of the invention may be better understood by referring to the following description in conjunction with the accompanying drawings in which.

DETAILED DESCRIPTION

Figure 1:
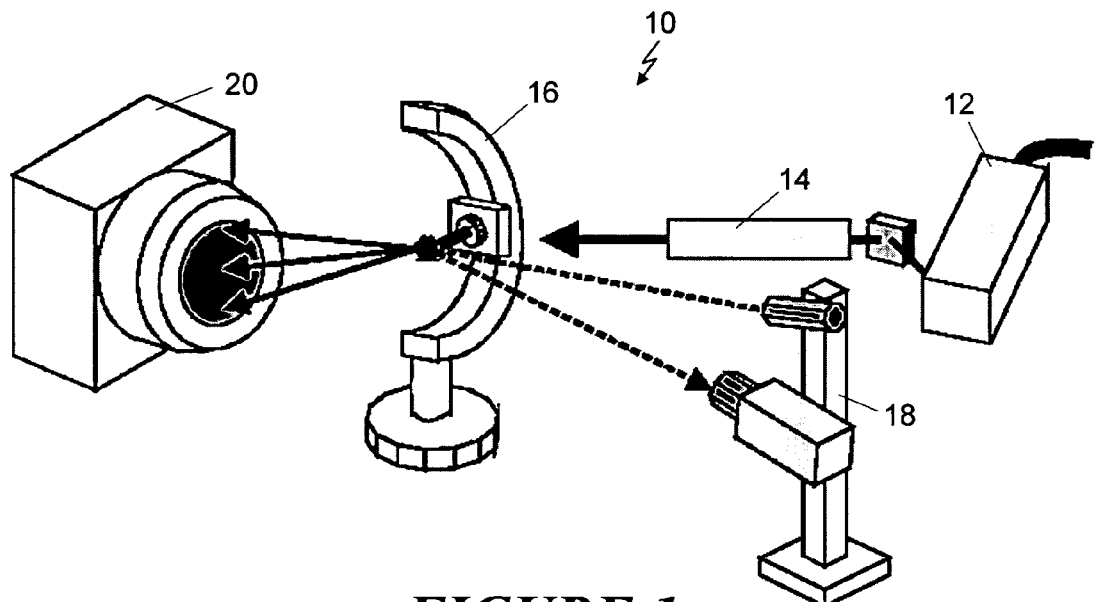
FIG. 1 is a schematic view of a typical prior art two-dimensional x-ray diffraction detection system.
Figure 2:
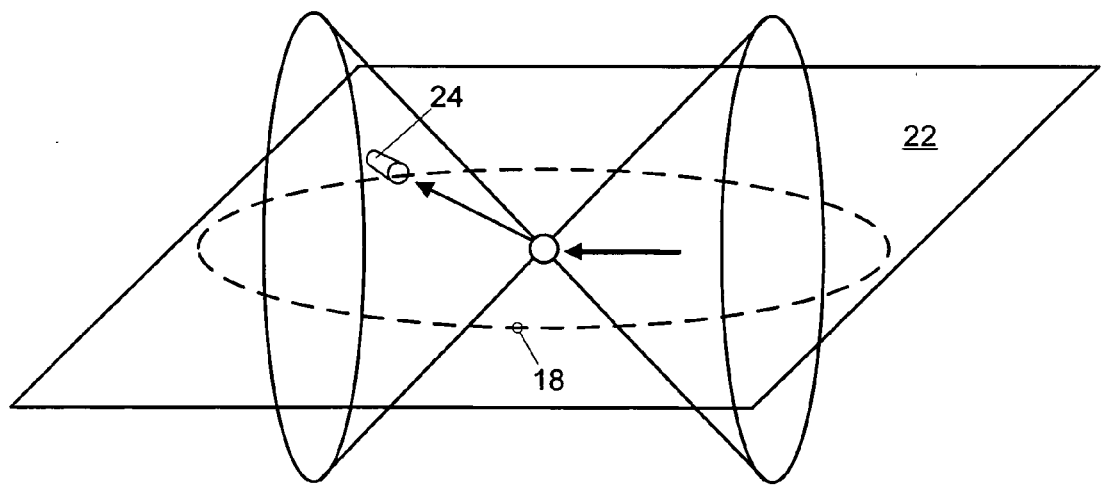
FIG. 2 is a schematic view of a prior art arrangement that uses a point detector in an x-ray diffraction system.
Figure 3:
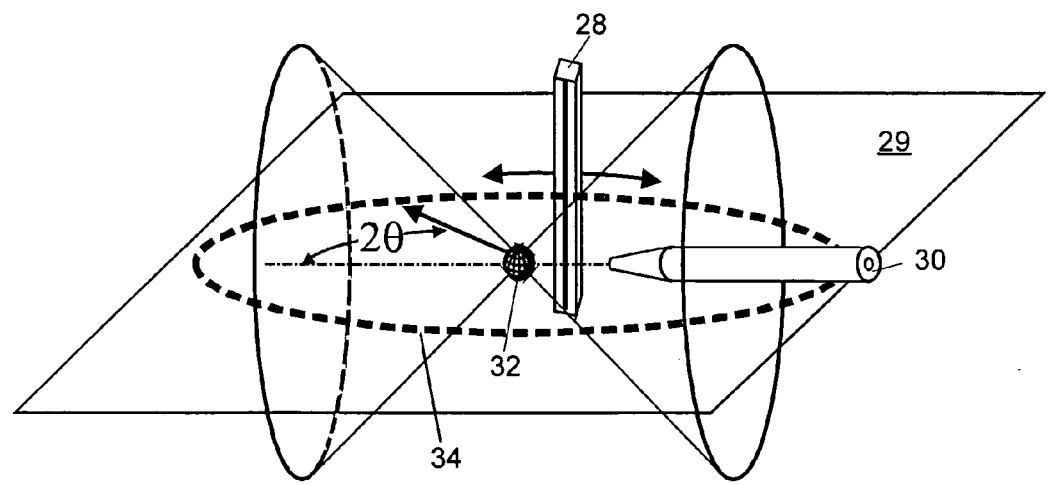
FIG. 3 is a schematic view of the basic arrangement of a scanning line detection system according to the present invention.

Shown in FIG. 3 is a schematic view of a diffractometer that uses a line detector 28 mounted perpendicularly to a diffractometer plane 29. An x-ray source 30 (which includes the necessary conditioning optics) directs a beam of x-rays toward sample 32. The x-rays are diffracted by the sample in both forward and backward directions. The line scanner 28 rotates around the sample, following the detection circle 34. Unlike a point detector, however, the line detector collects information all along a perpendicular line that sweeps through the detection circle, thus providing two-dimensional data.

Figure 4:
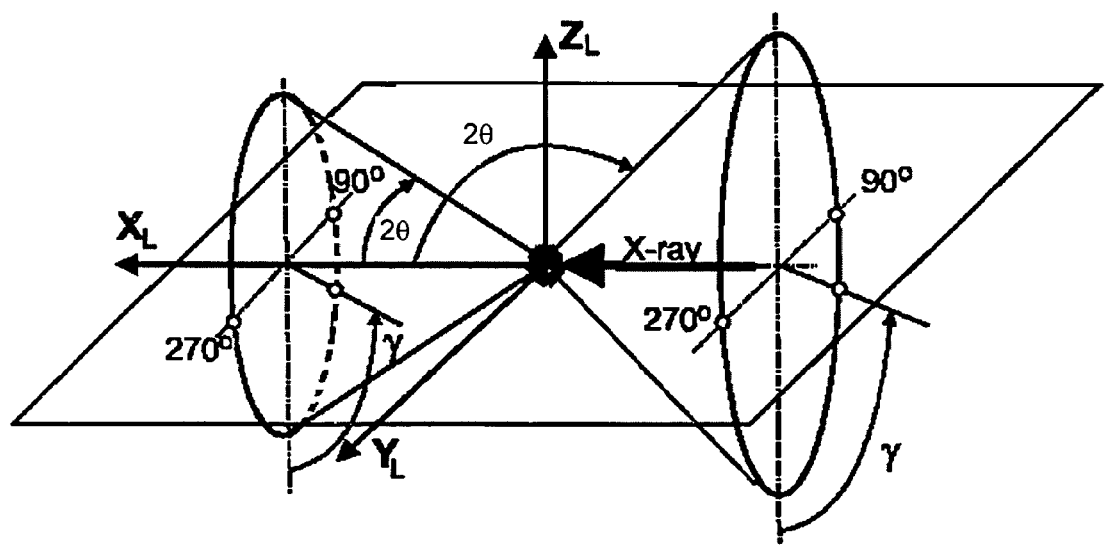
FIG. 4 is a graphical view of the various geometric relationships within a system like that of FIG. 3.

In order to analyze the two-dimensional diffraction data collected by a scanning line detector, a coordinate system is established relative to the various diffraction angles and detector pixel positions. FIG. 4 shows the geometric definition of diffraction cones in the laboratory coordinate system, $X_L Y_L Z_L$. The origin of the coordinates is also called the goniometer center or the instrument center. The direct x-ray beam propagates along the $X_L$ axis, which is also the rotation axis of the diffraction cones. The apex angles of the cones are determined by 2θ values given by the Bragg equation $\lambda=2d(\sin\theta)$, where λ is the wavelength and d is the spacing between adjacent crystal planes. The apex angles are twice the 2θ values for forward reflection (2θ≦90°) and twice the values of 180°-2θ for backward reflection (2θ>90°). The $X_L$-$Y_L$ plane is the diffractometer plane. The γ angle defines a position on the diffraction cone relative to a particular location along the $X_L$ axis. The γ angle is measured in the $Y_L$-$Z_L$ plane at the particular $X_L$ position, with the angle being taken from the $-Z_L$ direction to the desired point on the cone. The conventional diffractometer plane corresponds to γ=90° on the negative $Y_L$ side and γ=270° in the positive $Y_L$ side. The γ and 2θ angles together form a kind of spherical coordinate system which covers all the directions from sample (i.e., from the goniometer center). The γ-2θ system is fixed in the laboratory systems $X_L Y_L Z_L$, which is independent of the sample orientation in the goniometer. This is a very important concept when we deal with 2D diffraction data.

An ideal detector for measuring the diffraction pattern in 3D space would have a spherical detecting surface covering all the diffraction directions in 3D space, with the sample is in the center of the sphere. The incident x-ray beam points toward the center of the sphere from the direction 2θ=π. In practice, such an ideal spherical detector does not exist. However, there are many 2D detector technologies available, including photographic film, CCD, image plate (IP) and multi-wire proportional counter (MWPC). The detection surface can be a portion of a sphere or a cylinder, a surface curved in some other way, or a flat surface. The curved detector surfaces are normally designed for a fixed sample to detector distance, while a flat detector has the flexibility to be used at different sample-to-detector distances.

Figure 5:
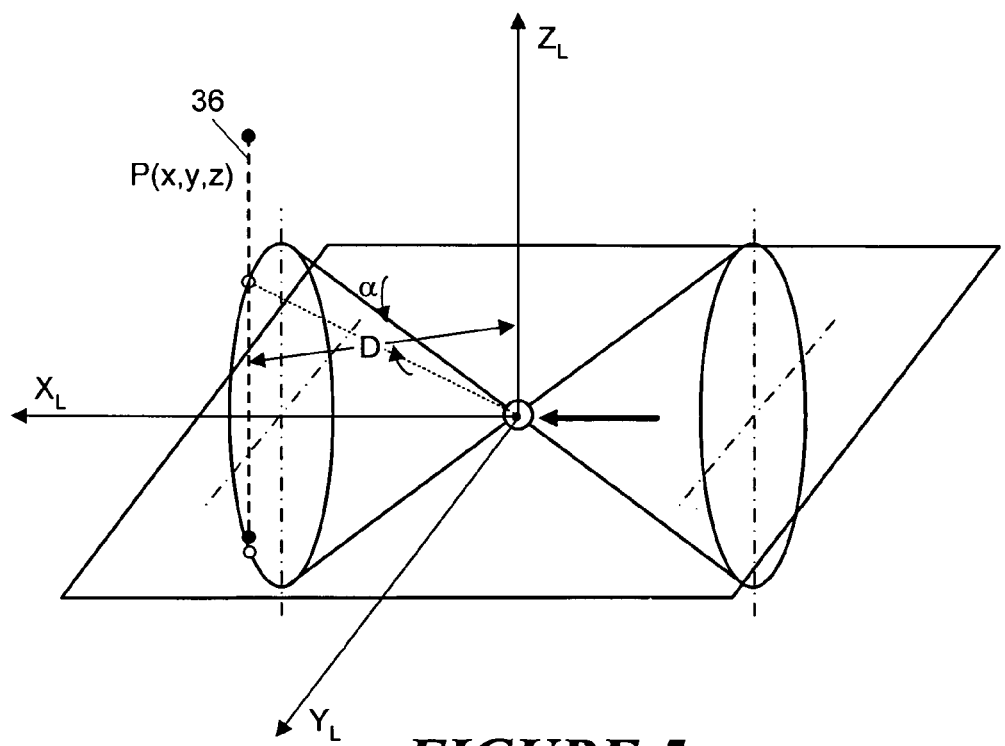
FIG. 5 is a graphical view showing the use of a coordinate system within a scanning line detector system according to the present invention.

In the present invention, a two-dimensional detector is simulated by the use of the scanning line detector. In the embodiment shown in FIG. 3, a two-dimensional, cylindrical scanning surface is simulated by the scanning line detector in order to analyze the two-dimensional diffraction data, 2θ and γ angles in the diffraction space should be calculated for each pixel in the diffraction frame. As is shown in FIG. 5, a position of the line detector (indicated by a dashed "detector" line 36 in the figure) is determined by the detector distance D and the detector swing angle α. The detector distance D is measured between the detection line and instrument center within the diffractometer plane. The detector swing angle α is defined as the angle measured in the diffractometer plane between the $X_L$ axis and the line extended from the origin to the detector. For a given point on the line detector, P(x,y,z), the position of the point in the diffraction space is determined by (x, y, z) in the laboratory coordinates, where z is given as the distance from the diffractometer plane to the point on the line detector and, $x = D \cos\alpha$ $y = D \sin\alpha$ The γ and 2θ angles of each pixel can be calculated from:

$$\gamma = \begin{cases} \arccos\dfrac{-z}{\sqrt{z^2 + D^2\sin^2\alpha}} & -180° \leq \alpha < 0° \\ 180° + \arccos\dfrac{z}{\sqrt{z^2 + D^2\sin^2\alpha}} & 0° \leq \alpha \leq 180° \end{cases}$$

$$\text{and } 2\theta = \arccos\dfrac{D\cos\alpha}{\sqrt{D^2 + z^2}}$$

Figure 6:
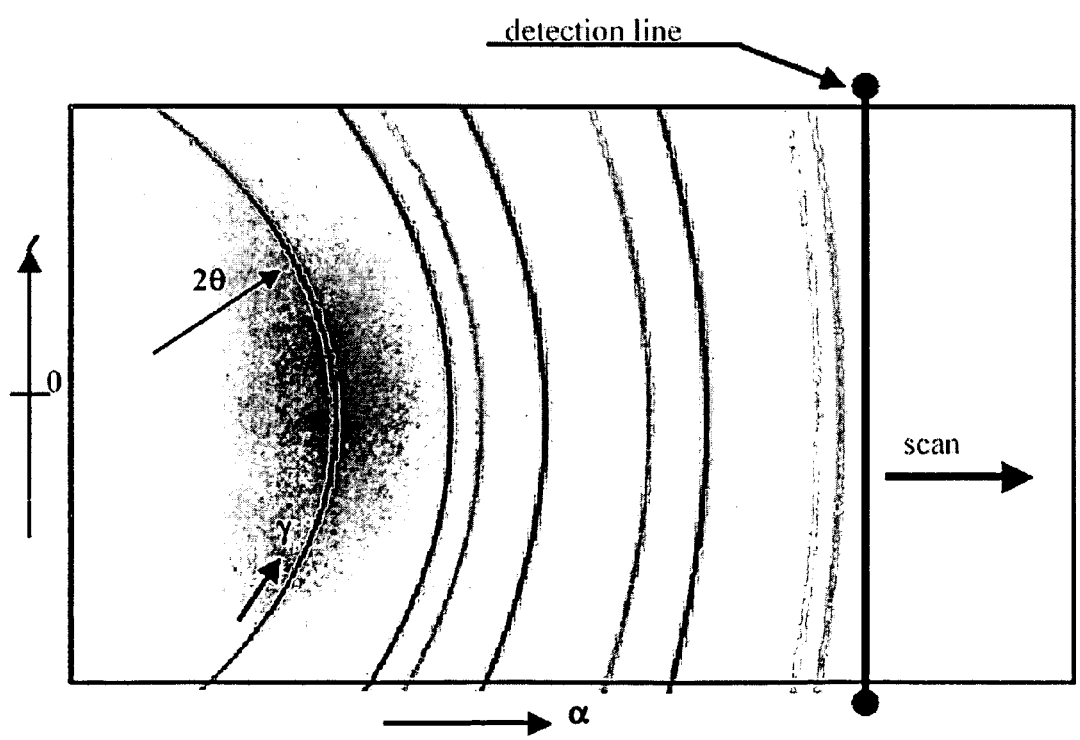
FIG. 6 is a schematic view of diffraction data collected with a line detector according to the present invention.

During data collection, the line detector scans along the detection circle while collecting diffraction signals. FIG. 6 is an illustration of the data collected with a line detector. The line signals at sequential detector positions form a two-dimensional diffraction image. The horizontal axis corresponds to the detector swing angle α, and the vertical axis corresponds to the pixel height z. The aforementioned equations convert each pixel position (in α and z) to a point in diffraction space (γ and 2θ). The two-dimensional diffraction image can then be displayed and analyzed using the two-dimensional diffraction theory. Other equations may be used to calculate the diffraction space parameters (γ and 2θ) for the same geometry or different geometry. All consequent data integration for phase identification, stress analysis, texture analysis and other diffraction applications are based on this conversion.

There are many advantages of two-dimensional diffraction with line detector. In addition to having most of the functions available with a conventional two-dimensional detector, additional advantages are also realized. For one, the cost of a line detector is typically much less than an area detector, making it more affordable to many users. The line detector may also provide higher resolution than a conventional two-dimensional detection method for a number of reasons. Firstly, a line detector can be built with smaller pixel size than a two-dimensional detector. Secondly, the line scan step using a typical goniometer can be much smaller than the pixel size of a typical two-dimensional detector. Thirdly, it is possible to add a slit along the line direction to control the detection line width.

Figure 7:
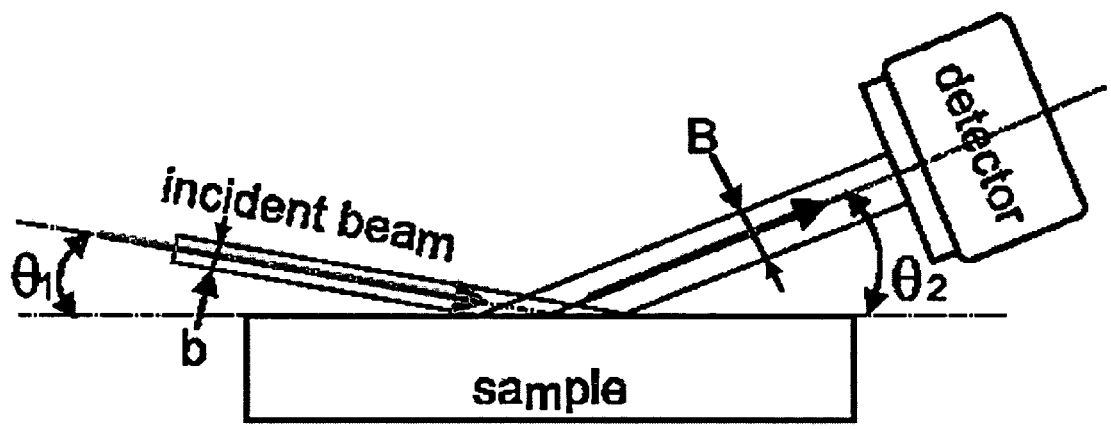
FIG. 7 is a graphical view showing geometric relationships in a two-dimensional diffraction system using a two-dimensional detector in reflection mode.

The line scanning detector of the present invention also has the advantage of eliminating a defocusing effect which occurs with x-ray diffraction conducted using a low angle of incidence in the x-ray beam. FIG. 7 shows the geometry of two-dimensional diffraction with a 2D detector in reflection mode. A defocusing effect is observed with a low incident angle over a flat sample surface. Looking at the cross section on the diffractometer plane, the defocusing effect with reflection mode diffraction can be expressed as:

$$\frac{B}{b} = \frac{\sin\theta_2}{\sin\theta_1} = \frac{\sin 2\theta - \omega}{\sin\omega}$$

where $\theta_1$ is the incident angle, b is the incident beam size and B is diffracted beam size (based on projection on the diffractometer plane). The ratio of B to b is the defocusing factor. The diffracted beam is focused to the detector when $\theta_2 < \theta_1$. The defocusing effect increases with increasing $\theta_2$ or decreasing $\theta_1$. The maximum defocusing appears at $\theta_2 = 90°$. For a $\theta/2\theta$ configuration, the incident angle $\omega$ is used in the equation. With line scan diffraction, the incident angle $\theta_1$ can change simultaneously with the detector scan so to keep $\theta_1 = \theta_2$. This eliminates the defocusing effect by maintaining a constant defocusing factor of 1.

In one particular embodiment of the present invention, an air scatter shield may be used to reduce background noise in the detector caused by air scatter. Air scatter results from x-rays being scattered by air molecules between the x-ray source and the sample, or even between the diffracted x-rays and the detector. Air scatter with a two-dimensional detector has a significant contribution to the intensity background. However, with a line detector, air scatter may be blocked by an air scatter shield.

Figure 8:
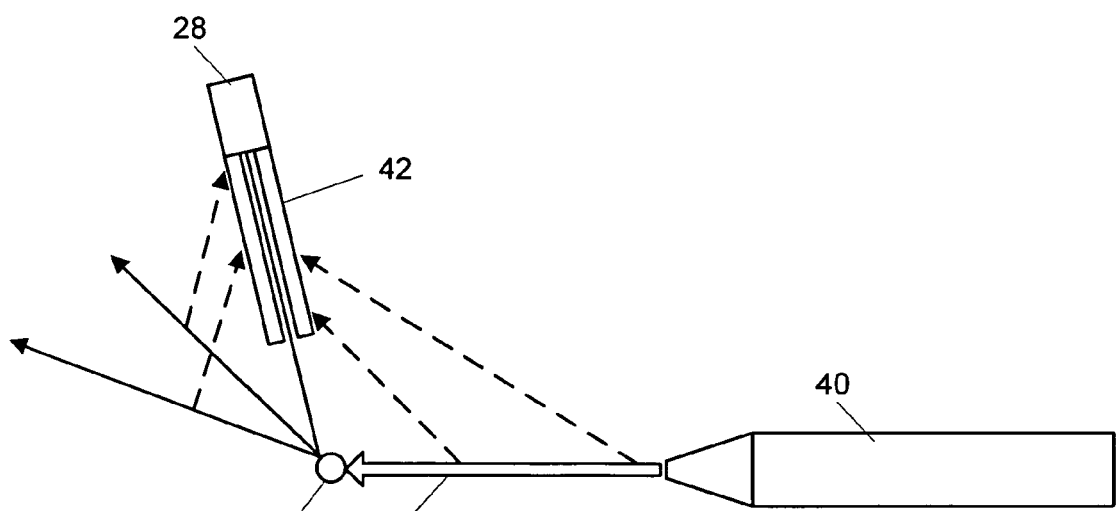
FIG. 8 is a schematic view of a detector that may be used with the present invention and that has a scatter shield that prevents air-scattered x-ray energy from reaching the detection elements.

As shown in FIG. 8, an initial x-ray beam 38 exits the collimator that conditions the x-rays from an x-ray source. The x-ray beam 38 encounters sample 32 and is diffracted accordingly. The solid lines in the figure indicate (schematically) the diffracted portions of the x-ray beam. However, there are also portions of the initial x-ray beam, as well as the diffracted x-rays, that are scattered by air molecules toward the line detector 28. These scattered x-rays are represented in the figure (schematically) by the dashed lines. If the scattered x-rays reach the detection pixels of the detector, they can result in erroneous low-level signals that act as background noise.

The view of the line detector 28 in FIG. 8 is along the z-direction, that is, along the longitudinal dimension of the detector. In this embodiment, the front of the detector is outfitted with a scatter shield 42 that blocks most of the x-ray energy that is scattered in the direction of the line detector 28. The scatter shield may be shaped like a slit that extends the length of the line detector 28, and opens in the direction faced by the detector for detection purposes. In this way, the desired diffracted x-ray energy will reach the detector, while the undesired scattered x-rays will be blocked.

It is also possible with the line detector of the present invention to make use of a diffracted beam monochromator. The spectrum impurity of the incident beam and/or radiation fluorescence from the sample are sources of intensity background with a two-dimensional detector, for example, when Cu—Kα radiation is used for iron or ferrous alloys. Most two-dimensional detectors have a very limited energy resolution and it is impossible to add a diffracted beam monochromator in front of a two-dimensional detector. However, it is possible to use a specially designed monochromator in front of the line detector of the present invention.

Figure 9:
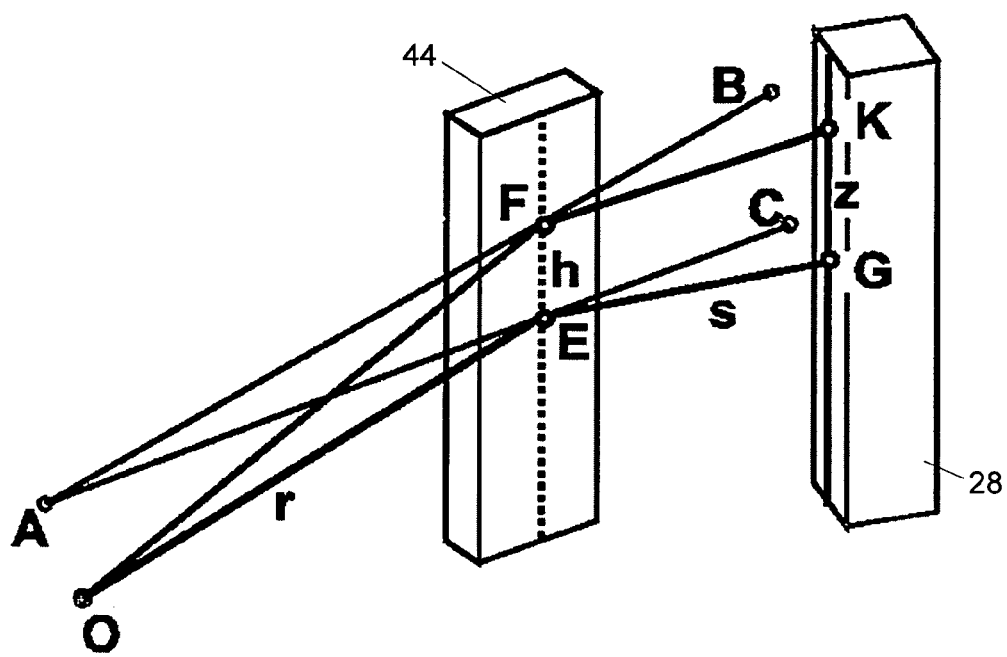
FIG. 9 is a schematic view of an embodiment of the invention in which a monochromator is used to condition the diffracted x-ray energy before it reaches the detection elements.

FIG. 9 is an illustration showing a multilayer mirror 44 used as a monochromator with the line detector. The lines OE and EG represent the path of a diffracted beam within the diffractometer plane. The path goes from the sample to the mirror and from the mirror to the line detector. The line AC is also in the diffractometer plane, and represents a projection of OE and EG that follows the surface of the mirror. The lines OF and FK represent the path of a diffracted beam that is outside of the diffractometer plane. Again, the path goes from the sample to the mirror and from the mirror to the line detector, but this path is above the diffractometer plane. The line AB is also outside of the diffractometer plane, and represents a projection of OF and FK that follows the surface of the mirror.

In this geometric model, the distance between the sample and the mirror in the diffractometer plane is r, and the distance between the mirror and detector in the diffractometer plane is s. However, this is different than the distance between O and F, since F is located above the diffractometer plane. On the surface of the mirror 44, the distance between F and E is h, and on the line detector the distance between K and G is z. These distances are related as follows:

$$z = \frac{r+s}{r} h$$

The angles $\angle OEA$ and $\angle GEC$ are the Bragg angle of the mirror in the diffractometer plane, $\theta_0 = \angle OEA = \angle GEC$. The angles $\angle OFA$ and $\angle KFB$ are the Bragg angle of the mirror at the position h above the diffractometer plane, $\theta_H = \angle OFA = \angle KFB$. $\theta_H$ is given as $$\sin\theta_h = \frac{r}{\sqrt{r^2 + h^2}} \sin\theta_0$$

The mirror should have a variable d-spacing to compensate for these different angles. The corresponding d-spacing (i.e., the layer spacing) of the multilayer mirror is given as:

$$d = \frac{\sqrt{r^2 + h^2}}{r} d_0$$

where $d_0$ is the d-spacing of the mirror at the diffractometer plane. Thus, a multilayer mirror designed with such a d-spacing distribution can be used as an effective monochromator in front of the line detector.

Figure 10:
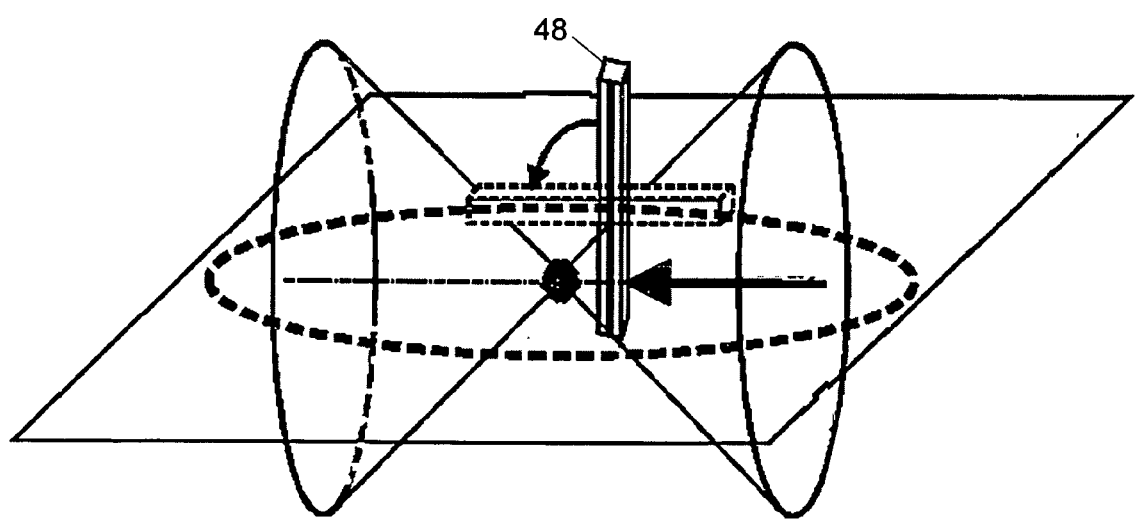
FIG. 10 is a schematic view of a detector according the present invention, wherein the detector may be rotated along an axis parallel to a direction along which x-ray energy is diffracted.

The line detector apparatus of the present invention can also be mounted in a mechanism which allows an easy switch between line scan mode and a conventional mode. Shown in FIG. 10 is an arrangement in which the line scanner 48 is rotatable between two mutually perpendicular orientations. In the position for line scan mode (shown in solid lines), the detection line is perpendicular to the diffractometer plane. In the conventional mode (shown in broken lines) the detection line is in the diffractometer plane itself. Those skilled in the art will recognize that other orientations are likewise possible.

In another variation of the present invention, the line detector can be used alternatively as a conventional point detector. By using a limited detection region and corresponding divergent slits, anti-scatter slit and soller slits, the line detector can function as a point detector for Bragg-Brentano parafocusing geometry and parallel beam geometry.

Those skilled in the art will also recognize that the use of a line detector allows a lot of flexibility in the simulation of different two-dimensional detector surfaces. For example, some two-dimensional diffraction systems use a cylindrically-shaped two-dimensional detector, such as a cylindrical image plate. Such a cylindrical detector is designed for a fixed radius of the cylinder. However, while the trace of a scanning line detector can be chosen to mimic a particular cylindrical shape, the radius of the cylinder can be changed by changing the detector distance D. A user can choose a short distance for large angular coverage or long distance for better angular resolution.

While the invention has been shown and described with reference to certain embodiments thereof, it will be recognized by those skilled in the art that various changes in form and detail may be made herein without departing from the spirit and scope of the invention as defined by the appended claims.

What is claimed is:

1. An x-ray diffraction analysis system for analyzing a sample located at a sample location that intersects a diffractometer plane, the system comprising:
   a source of x-ray energy directed toward the sample;
   an x-ray detector having individual detection elements arranged in an elongate shape to form a detection area that extends substantially linearly along a longitudinal dimension of the detector, wherein the x-ray detector moves along a detection circle centered about an axis that passes through the sample location perpendicular to the diffractometer plane so as to collect x-ray diffraction data across a multidimensional space; and
   a mechanism that generates a two-dimensional x-ray diffraction pattern from collected x-ray diffraction data.

2. A system according to claim 1 wherein the detection elements of the detector are arranged in a substantially straight line.

3. A system according to claim 1 wherein the sample intersects a diffractometer plane, and wherein the detector follows a path that is parallel to the diffractometer plane.

4. A system according to claim 3 wherein the detector is movable in a direction perpendicular to the diffractometer plane while following the path parallel to the diffractometer plane.

5. A system according to claim 1 further comprising a slit positioned in front of the detection elements of the detector that limits the detection line width.

6. A system according to claim 1 further comprising a scatter shield that moves with the detector and that shields the detector from scattered x-ray radiation along directions outside of an selected x-ray diffraction range.

7. A system according to claim 1 further comprising a monochromator that redirects diffracted x-ray energy toward the detector, the monochromator limiting the redirected x-ray energy to a predetermined wavelength range.

8. A system according to claim 7 wherein the monochromator comprises a multilayer mirror.

9. A system according to claim 8 wherein the multilayer mirror has a layer d-spacing that varies along a direction parallel to the longitudinal dimension of the detector.

10. A system according to claim 1 wherein the detector may be positioned in any of a plurality of rotational orientations about an axis parallel to a plane containing the detection circle.

11. A system according to claim 1 wherein a distance between the detector and the sample may be changed to change an angular resolution of the detector.

12. An x-ray diffraction analysis system according to claim 1 wherein the two-dimensional x-ray diffraction pattern comprises Debye rings.

13. A method of performing an x-ray diffraction analysis of a sample located at a sample location that intersects a diffractometer plane, the method comprising:

directing x-ray energy toward the sample with an x-ray source;
detecting x-ray energy diffracted from the sample with an x-ray detector having an elongate shape such that individual detection elements of the detector are arranged substantially linearly; and
moving the x-ray detector along a detection circle centered about an axis that passes through the sample location perpendicular to the diffractometer plane so as to collect x-ray diffraction data across a multidimensional space; and
generating a two-dimensional x-ray diffraction pattern from collected x-ray diffraction data.

14. A method according to claim 13 wherein the detection elements of the detector are arranged in a substantially straight line.

15. A method according to claim 13 wherein the sample intersects a diffractometer plane, and wherein moving the detector comprises moving the detector along a path that is parallel to the diffractometer plane.

16. A method according to claim 15 wherein the detector is movable in a direction perpendicular to the diffractometer plane while following the path parallel to the diffractometer plane.

17. A method according to claim 13 further comprising limiting the detection line width with a slit positioned in front of the detection elements of the detector.

18. A method according to claim 13 further comprising shielding the detector from scattered x-ray radiation along directions outside of an anticipated x-ray diffraction range with a scatter shield that moves with the detector.

19. A method according to claim 13 further comprising redirecting diffracted x-ray energy toward the detector with a monochromator that limits the redirected x-ray energy to a predetermined wavelength range.

20. A method according to claim 19 wherein the multilayer mirror has a layer d-spacing that varies along a direction parallel to a longitudinal dimension of the detector.

21. A method according to claim 13 wherein the detector may be positioned in any of a plurality of rotational orientations about an axis parallel to a plane containing the detection circle.

22. A method according to claim 13 further comprising changing a distance between the detector and the sample to change an angular resolution of the detector.

23. A method according to claim 13 wherein the two-dimensional x-ray diffraction pattern comprises Debye rings.

24. An x-ray diffraction analysis system for analyzing a sample located at a sample location that intersects a diffractometer plane, the system comprising:
   a source of x-ray energy directed toward the sample; and
   an x-ray detector having individual detection elements arranged in an elongate shape to form a detection area that extends in a substantially straight line along a longitudinal dimension of the detector, wherein the x-ray detector moves along a detection circle that is parallel to the diffractometer plane and that is centered about an axis that passes through the sample location, so as to collect x-ray diffraction data across a multidimensional space; and
   a mechanism that generates a two-dimensional x-ray diffraction pattern from collected x-ray diffraction data.

25. An x-ray diffraction analysis system according to claim 24 wherein the two-dimensional x-ray diffraction pattern comprises Debye rings.

* * * * *